United States Patent [19]

Huebner

[11] Patent Number: 5,702,472
[45] Date of Patent: Dec. 30, 1997

[54] PHALANGEAL FINGER JOINT PROSTHESIS AND METHOD

[76] Inventor: Randall J. Huebner, 18650 SW. Hart Rd., Aloha, Oreg. 97005

[21] Appl. No.: 773,968

[22] Filed: Dec. 26, 1996

[51] Int. Cl.$^6$ ........................................................ A61F 2/42
[52] U.S. Cl. .................................................. 623/21; 623/18
[58] Field of Search ................................ 623/18, 20, 21

[56] References Cited

U.S. PATENT DOCUMENTS

| | | | |
|---|---|---|---|
| 3,992,726 | 11/1976 | Freeman et al. | 623/21 |
| 4,011,603 | 3/1977 | Steffee | 623/21 |
| 4,085,466 | 4/1978 | Goodfellow et al. | |
| 4,224,696 | 9/1980 | Murray et al. | |
| 4,224,697 | 9/1980 | Murray et al. | |
| 4,276,660 | 7/1981 | Laure | |
| 4,586,933 | 5/1986 | Shoji et al. | 623/20 |
| 4,634,445 | 1/1987 | Helal | 623/21 |
| 4,759,766 | 7/1988 | Buettner-Janz et al. | 623/17 |
| 4,759,768 | 7/1988 | Hermann et al. | 623/21 |
| 5,007,933 | 4/1991 | Sidebotham et al. | 623/20 |
| 5,011,497 | 4/1991 | Persson et al. | 623/21 |
| 5,092,896 | 3/1992 | Meuli et al. | 623/21 |
| 5,133,761 | 7/1992 | Krouskop | 623/21 |
| 5,246,460 | 9/1993 | Goodfellow | 623/20 |
| 5,290,314 | 3/1994 | Koch et al. | 623/21 |
| 5,458,647 | 10/1995 | Brochier et al. | 623/21 |
| 5,556,432 | 9/1996 | Kubein-Meesenburg et al. | 623/18 |

FOREIGN PATENT DOCUMENTS 9011062 10/1990 WIPO ............................. 623/18

Primary Examiner—Randy C. Shay
Attorney, Agent, or Firm—Kolisch, Hartwell, Dickinson, McCormack & Heuser

[57] ABSTRACT

A phalangeal joint prosthesis for replacing damaged interphalangeal finger joints. The prosthesis includes first and second pins, each having an elongate shaft for inserting into the articulating end of a first or a second phalange on respective sides of a finger joint. Each pin further includes a head with a lower surface mounted on the shaft and a convex cylindrically-shaped bearing surface that is opposite the lower surface and defines an axis of curvature. The prosthesis further includes a spacer configured to be disposed between the heads of the first and the second pins. The spacer has opposed bearing surfaces that are each configured to mate with the bearing surface of one of the heads so that the bearing surfaces of the heads are generally oriented toward each other. The spacer couples the first and second pins in a spaced relationship with parallel axes of curvature to permit the prosthesis to flex and extend in a single plane while constraining abduction, adduction and rotation of the prosthesis. Each of the bearing surfaces of the spacer has a concave cylindrical configuration that corresponds to the configuration of the bearing surface of the head that it receives.

27 Claims, 2 Drawing Sheets

PHALANGEAL FINGER JOINT PROSTHESIS AND METHOD

FIELD OF THE INVENTION

The present invention relates generally to joint prostheses. More particularly, it is directed to a phalangeal finger joint prosthesis and method of using the same.

BACKGROUND OF THE INVENTION

Fingers are comprised of two types of bones: metacarpals, which are connected to the carpus of a hand, and phalanges, a first of which is connected to the end of each metacarpal opposite the carpus and one or two others that are connected to the first in an end-to-end arrangement. The thumb has two phalanges, while the second through fifth fingers of a hand have three. Each of the end-aligned bones in a finger form a joint that provides for movement of the finger. A metacarpophalangeal joint includes the articulating ends of a metacarpal and first phalange and is capable of flexing and extending, as well as abducting and adducting, where the joint is moved respectively away from or toward the medial longitudinal axis of the hand. Phalangeal (or interphalangeal) joints are formed between adjacent phalanges and should flex and extend, but not abduct or adduct. Neither joint should allow either of the bones comprising the joint to rotate about its respective longitudinal axis.

The joints of the hand may be damaged through injury or disease. When the degree of deterioration or destruction is severe enough, the joint must be replaced. Therefore, there is a need for a phalangeal finger joint prosthesis that can be used to replace a damaged or deteriorated phalangeal joint.

When a prosthetic finger joint is implanted into a finger, portions of each of the articulating ends of the original joint must be resetted to provide room for the prosthesis. Resecting at least a portion of the ends of each phalange forms a cavity into which the prosthesis may be placed. It is desirable to minimize the amount of bone that must be resected. In addition, it is important that the prosthesis generally resemble the size and shape of the resected portions so that the range of motion of the prosthetic joint is not limited and so that the ligaments, tendons and nerves adjacent the prosthesis are not damaged or otherwise impaired.

A further consideration when implanting a prosthetic finger joint is the need for the ligaments surrounding the new joint to have a desired amount of tension. While a phalangeal joint should not freely abduct or adduct, it should allow a slight degree of rocking when lateral forces are applied to the finger. If the prosthesis is longer than the original joint, however, the ligaments will have excess tension, and the full range of motion of the joint will be constrained. In addition, when the ligaments have more than the desired amount of tension, lateral forces may strain or damage these ligaments. On the other hand, when the prosthesis is smaller than the original joint, the tension in the ligaments will be insufficient, and the joint will abduct and adduct. This lateral pivoting of the joint can cause excessive wear and damage to the prosthesis, as well as to the ligaments surrounding the prosthesis. Play in the joint also increases the chance of dislocation of the joint.

It is therefore an object of the present invention to provide a phalangeal joint prosthesis that enables flexion and extension while constraining abduction, adduction and rotation.

It is another object of the present invention to provide a phalangeal joint prosthesis that consists of relatively few components and minimizes the amount of bone that must be resected.

Yet another object of the present invention is to provide a phalangeal finger joint replacement kit for replacing phalangeal joints of various sizes and shapes with which the ligament tension in the joint can be adjusted.

These and other objects and advantages will be more clearly understood from a consideration of the accompanying drawings and the following description of the preferred embodiments.

SUMMARY OF THE INVEMTION

The present invention is a phalangeal joint prosthesis for replacing damaged interphalangeal finger joints. In the preferred embodiment, the prosthesis includes first and second pins, each having an elongate shaft for inserting into the articulating end of a first or a second phalange on respective sides of a finger joint. Each pin further includes a head with a lower surface mounted on the shaft and a convex cylindrically-shaped bearing surface that is opposite the lower surface and defines an axis of curvature. The heads are configured to generally correspond to the shape of the ends of the phalanges.

The prosthesis further includes a spacer configured to be disposed between the heads of the first and the second pins. The spacer has opposed bearing surfaces configured to mate with the bearing surfaces of the heads so that the bearing surfaces of the heads are generally oriented toward each other. The spacer couples the first and second pins in a spaced relationship with parallel axes of curvature to permit the prosthesis to flex and extend in a single plane while constraining abduction, adduction and rotation of the prosthesis. Each of the bearing surfaces of the spacer has a concave cylindrical configuration that corresponds to the configuration of the bearing surface of the head that it receives.

The present invention also includes a phalangeal joint replacement kit that includes the previously described first and second pins and a multiplicity of spacers. The spacers are similar to the previously described spacer, however, they have various depths, or thicknesses, measured as the shortest distance between the bearing surfaces of each spacer.

Many other features, advantages and additional objects of the present invention will become apparent to those versed in the art upon making reference to the detailed description which follows and the accompanying sheets of drawings in which the preferred embodiments incorporating the principles of this invention are disclosed as illustrative examples only.

DETAILED DESCRIPTION OF THE PREFERRED EMBODIMENTS

Figure 1:
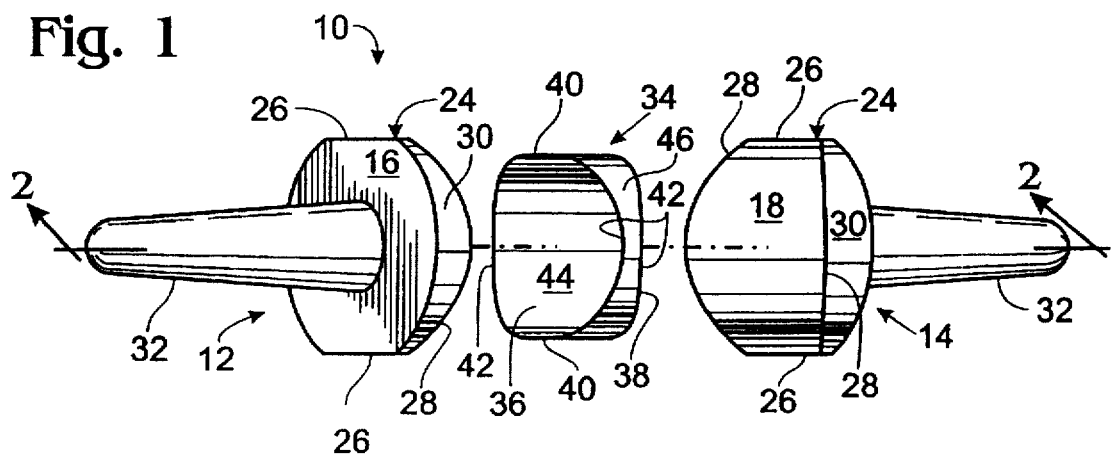
FIG. 1 is an exploded isometric view of a phalangeal joint prosthesis constructed according to the present invention.
Figure 2:
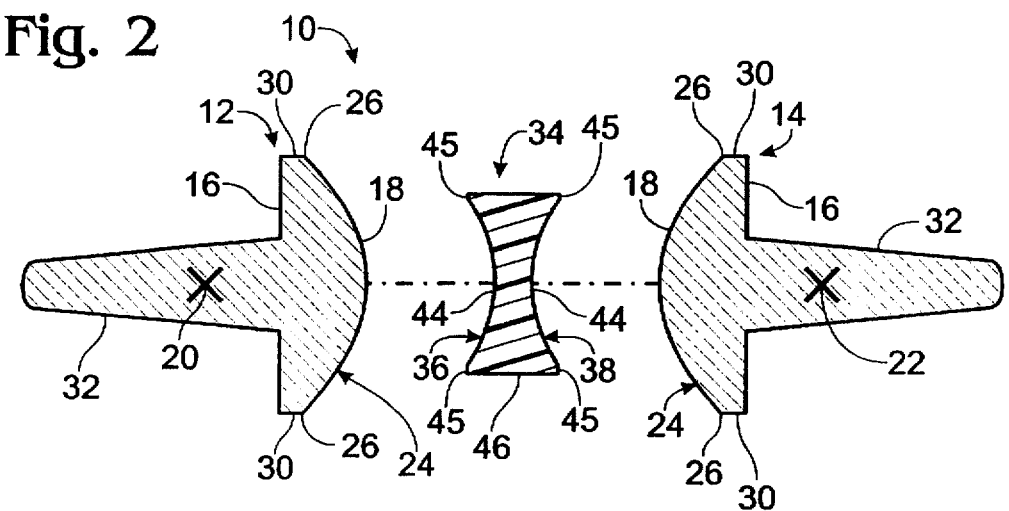
FIG. 2 is a cross-sectional view of the prosthesis of FIG. 1 taken along line 2—2 in FIG. 1.

A phalangeal finger joint prosthesis according to the present invention is shown generally at 10 in FIGS. 1 and 2. The prosthesis includes a pair of opposed bone-engaging members 12 and 14. Each member includes a lower surface 16 and a bearing surface 18 that is opposite lower surface 16 and defines an axis of curvature. The axes of curvature defined by the bearing surfaces are indicated generally in FIG. 2 with X's 20 and 22, respectively.

Bone-engaging members 12 and 14 are preferably pins, as shown in FIGS. 1 and 2. Because the pins are substantially identical, the following description will be made with reference to pin 12. Pin 12 has a head 24 that includes the previously described lower surface 16 and bearing surface 18. As shown, bearing surface 18 includes generally linear edges 26 parallel to the axis of a curvature 20 of bearing surface 18 and generally arcuate edges 28 transverse to that axis of curvature. The edges collectively define the perimeter of the bearing surface. Extending away from this perimeter, toward lower surface 16 is a side wall 30. Side wall 30 extends around at least a portion of the perimeter of head 24 adjacent bearing surface 18. Preferably, the side wall extends around the entire perimeter of the head.

The lower surface 16 has a generally planar configuration, as shown in FIG. 1. Furthermore, the lower surface includes a shaft 32 that extends away from bearing surface 18 of head 24. Shaft 32 is configured to be inserted into an end of one of the bones comprising the joint to be replaced. As shown, shaft 32 is centrally mounted on lower surface 16 and is conically tapered inwardly along its length as it extends away from head 24.

The prosthesis further includes a spacer, which is indicated generally at 34 in FIG. 1. Spacer 34 is configured to be disposed between the bone-engaging members, and specifically to be disposed between the bearing surfaces 18 of the bone-engaging members or pins 12 and 14. Spacer 34 includes opposed beating surfaces 36 and 38 that are each configured to receive the cylindrical bearing surface 18 of one of the heads 24 so that the bearing surfaces of the heads are generally facing each other. The spacer is configured to couple the first and second pins in a spaced relationship with parallel axes of curvature 20 and 22 to enable the prosthesis to flex and extend in a single plane while constraining abduction, adduction and rotation of the prosthesis.

As shown in FIGS. 1 and 2, each of the bearing surfaces 36 and 38 of spacer 34 has a concave cylindrical configuration that generally corresponds to the configuration of the bearing surface 18 of the head that it receives. Each bearing surface 36, 38 includes opposed generally linear edges 40 and opposed generally arcuate edges 42, that collectively define the perimeter of each bearing surface 36, 38. Each of the bearing surfaces further includes a race 44 along which the bearing surface 18 of one of the heads is received and can slidably pivot about its corresponding axis of curvature. Spacer 34 has a depth or thickness, which is measured as the shortest distance between beating surfaces 36, 38, and which is preferably in the range of approximately 1–5 millimeters.

As shown in FIG. 2, each beating surface 36, 38 is chamfered along its adjacent linear edges 40 to produce a pair of elongate shoulders 45. Although a spacer with bearing surfaces that do not include shoulders 45 is intended to be within the scope of the invention, it is preferable for the bearing surfaces of the spacer to include elongate shoulders adjacent the generally linear edges of the surfaces. Shoulders 45 reduce the likelihood of particulate being generated when pins 12 and 14 are repeatedly pivoted or slid against the bearing surfaces of the spacer. In addition, having shoulders 45 instead of an edged or pointed surface reduces the likelihood of damaging the tendons, ligaments or nerves surrounding the joint. The spacer further includes a side wall 46 extending between its bearing surfaces 36 and 38.

Figure 3:
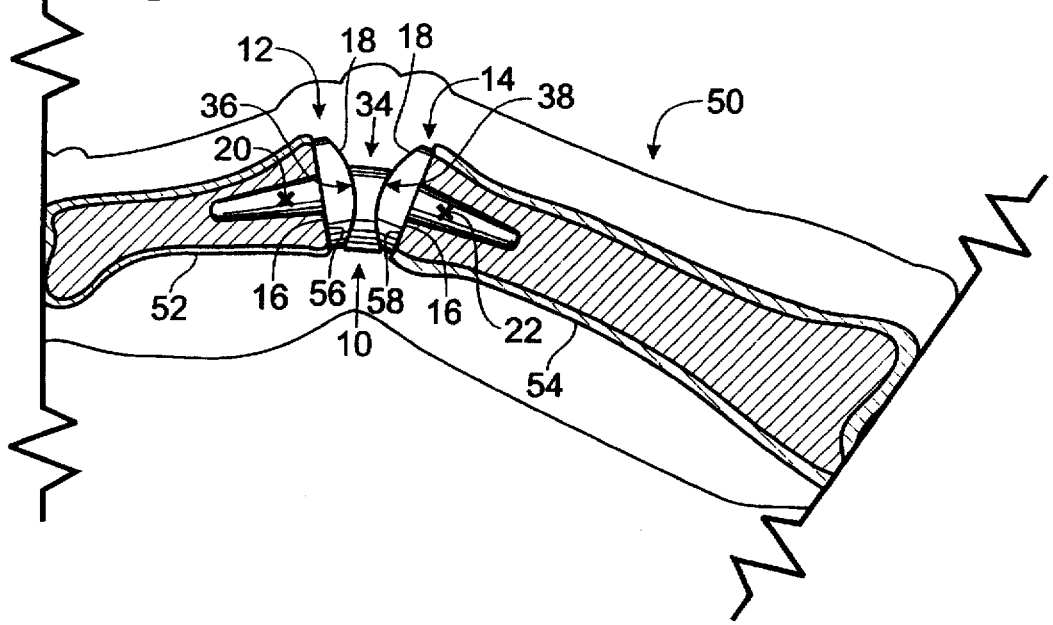
FIG. 3 is a partial cross-sectional side view of the prosthesis of FIG. 1 mounted on the articulating ends of opposed phalanges.

In FIGS. 2 and 3, the convex cylindrical configuration of bearing surfaces 18 on pins 12 and 14 and the concave cylindrical configuration of bearing surfaces 36, 38 on spacer 34 can be seen. The pins should be constructed of wear-resistant material that prevents the deposit of osseous tissue, such as stainless steel or titanium. The lower surface and shaft of each pin, however, may be roughened or coated to promote fusion with the surrounding bone when the prosthesis is implanted in a finger. The spacer should be constructed of ultra-high molecular weight polyethylene.

While bone-engaging members or pins 12 and 14 are shown in FIGS. 1–3 as being of relatively equal size, it should be understood that they may differ in size to correspond to the size of the ends of the bones to which they are mounted. Furthermore, it should be understood that the beating surfaces of the pins may vary in size and configuration. The bearing surfaces should, however, be of a suitable size to cooperate with the spacer to enable the prosthesis to flex and extend, while constraining the prosthesis from abducting, adducting and rotating. Although the general shape of pins 12, 14 and bearing surfaces 18 may vary, they should generally resemble the shape of an end of a phalange, while also being configured to reduce the likelihood of damages to ligaments, tendons and nerves surrounding the prosthesis once implanted in a finger. Similarly, spacer 34 and its bearing surfaces may also vary in size and configuration to generally correspond to the shape of the pins with which it is used.

A portion of a finger is generally indicated at 50 in FIG. 3. The portion includes at least a portion of a pair of articulating bones 52 and 54. Each bone has a proximal end, which is oriented towards the corresponding hand, and a distal end, which is oriented away from the hand. It should be understood that a finger joint includes the proximal end of a first bone and the distal end of an adjacent bone to form, respectively, the first and the second sides of the finger joint. The joint is surrounded by ligaments, tendons and nerves.

Preferably, the first and second bones described herein are phalanges. The invented prosthesis could, however, be used to replace a metacarpophalangeal joint if it is desirable to enable motion in one plane while constraining motion in all others. If so, the first and second bones will be a metacarpal and a phalange.

As shown in FIG. 3, a portion of the proximal end of bone 52 has been resetted to form a first mounting surface 56, and at least a portion of the distal end of bone 54 has been resetted to form a second mounting surface 58. As shown, pin 12 has been mounted on the first mounting surface. Specifically, shaft 32 has been inserted into bone 52, and the lower surface 16 is positioned to lie against first mounting surface 56. Second pin 14 has been mounted on the distal end of bone 54 in a similar fashion. Pins 12, 14 are mounted on bones 52, 54 so that their axes of curvature 20, 22 are parallel to the pivotal axis of the original joint. This enables the prosthesis to flex and extend in the same general plane as the original joint. Furthermore, although not shown in FIG. 3, it may be desirable to apply adhesive to at least a portion of the pins prior to inserting the pins into the corresponding bones.

Figure 4:
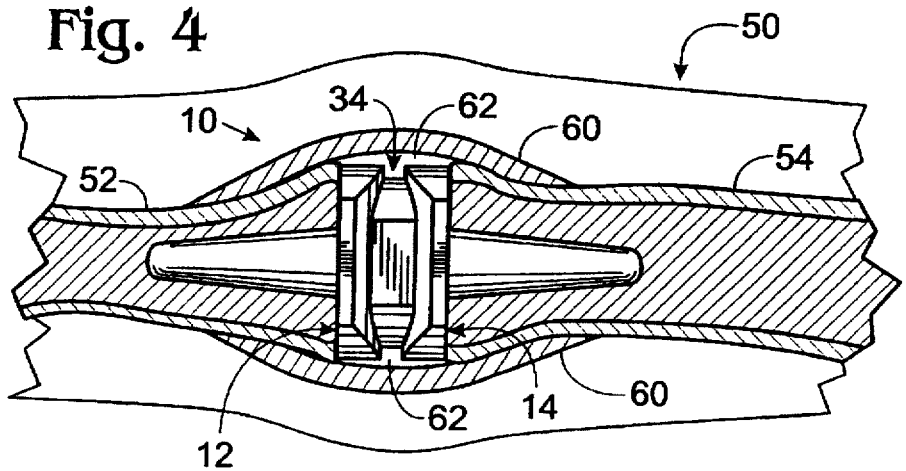
FIG. 4 is a partial cross-sectional top view of the prosthesis and phalanges of FIG. 3 with collateral ligaments shown on adjacent sides of the prosthesis.

In FIG. 4, ligaments 60 are shown on opposing sides of the prosthesis. It should be understood that ligaments 60 substantially encapsulate the joint, but have only been shown on adjacent sides of the joint for illustrative purposes. As shown, ligaments 60 are connected to and extend between the first and second bones 52 and 54 to surround the joint. In FIG. 4, one can see that ligaments 60 surround the joint, but still provide a small degree of lateral flexibility to the joint. For illustrative purposes only, this is represented by cavities 62 formed between the prosthesis and the ligaments.

Figure 5:
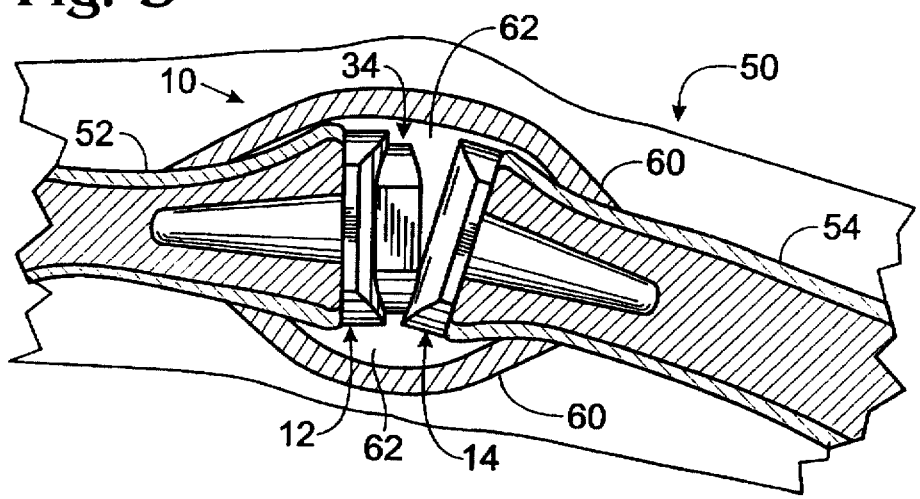
FIG. 5 is an alternate view of the prosthesis of FIG. 4, illustrating how abduction or adduction of the joint can occur when the desired tension is not present in the ligaments surrounding the prosthetic joint.

A small degree of lateral flexibility is important because it allows the joint to rock or pivot slightly sideways when an external lateral force is applied to the finger. Without this flexibility, there is an increased likelihood that the ligaments will be damaged by the applied force. Preferably, the prosthesis is sized to have this slight degree of flexibility when implanted into a finger and surrounded by ligaments. The prosthesis should not, however, have excessive lateral flexibility, which results when the prosthesis is much smaller than the amount of bone resected from the original joint. When this occurs, the prosthesis may abduct or adduct because there is too much slack in ligaments 60, as shown in FIG. 5. This lateral pivoting of pins 12 or 14 significantly increases the wear on the pins and spacer, as well as on the ligaments, tendons and nerves surrounding the prosthesis. Additionally, when the amount of slack in ligaments 60 is significant, it may be possible for spacer 34 to be dislocated from its position between the bearing surfaces of pins 12 and 14. Not only will this result in significant pain to the patient, but also it will render the prosthesis inoperable.

Figure 6:
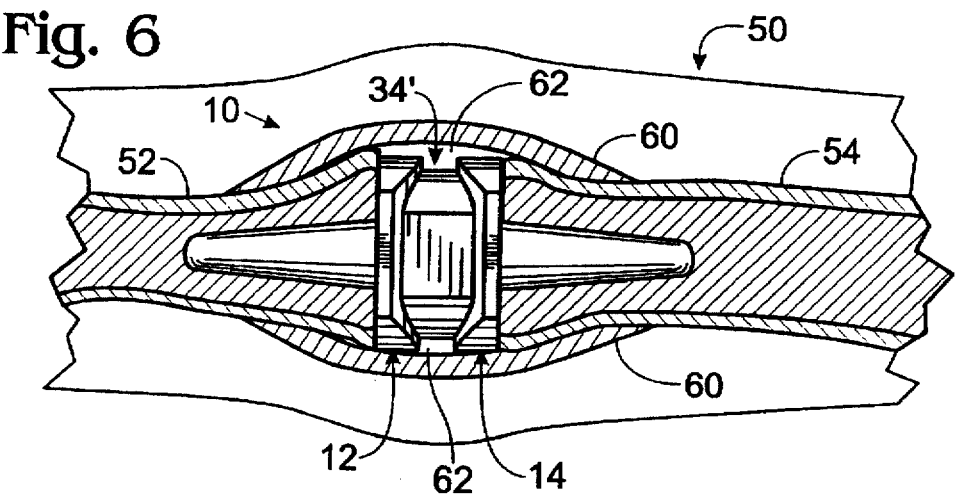
FIG. 6 is an alternate view of the prosthesis shown in FIG. 5, with a spacer having a larger depth to provide desired tension in the ligaments.

As discussed, spacer 34 may have various depths, measured as the shortest distance between bearing surfaces 36, 38. It is therefore possible to obtain desired tension in the ligaments surrounding the prosthesis by using a spacer with an appropriate depth. For example, when there is less than the desired amount of tension in the ligaments, such as in the ligaments surrounding the prosthesis shown in FIG. 5, the tension can be increased by using a spacer with a larger depth, such as spacer 34', which is shown in FIG. 6. Spacer 34' increases the overall size of the prosthesis and results in the ligaments having the desired tension. By comparing FIGS. 4 and 6, the reader can see that cavities 62, which illustrate the amount of flexibility in ligaments 60, are of relatively equal size in both figures, although the prostheses are of different size. It should be understood that similar adjustments could be made if there is too little flexibility in the prosthesis. Instead of choosing a spacer with a larger depth, such as spacer 34' which increases the tension in the ligaments, a spacer with a smaller depth should be selected to decreases the tension, thereby increasing the amount of flexibility in the prosthesis.

A second embodiment of the invention is a phalangeal finger joint replacement kit. The kit includes a first and second pin, such as the previously described pins 12 and 14. The kit further includes a multiplicity of spacers that are similar to the previously described spacer 34, although the spacers have various depths, measured as the shortest distance between the bearing surfaces of each spacer. Preferably, the kit includes a multiplicity of pins that vary in size and configuration.

By providing at least a first and second pin and a multiplicity of spacers, a user is able to implant the pins in the articulating ends of a finger joint, and then select a spacer that provides desired tension to the prosthesis. Furthermore, by providing a kit with a multiplicity of pins, as well as spacers, the user may select the pins and spacers that are sized to most closely correspond to the shape and size of the ends of the bones that are resected. A further advantage of the kit is that the mount of bone which must be resected prior to inserting the pins may vary from finger to finger. This is especially true when the degree of deterioration or damage to the bones is severe. Although it is preferable to minimize the amount of bone that must be resetted, severely deteriorated or damaged bones may require an increased amount of bone to be removed in order to provide a suitable mounting surface for the prosthesis.

To insert the previously described pair of pins 12, 14 and spacer 34 into a phalangeal finger joint that includes adjacent phalanges with articulating ends that define a pivotal axis, at least a portion of each of the articulating ends must be resetted to form mounting surfaces. The shaft of one of the phalanges is inserted into the end of one of the phalanges so that the lower surface of the corresponding pin is adjacent the mounting surface on that phalange and the axis of curvature of the head of the pin is parallel to the pivotal axis of the joint. Next, the second pin is inserted into the end of the other phalange so that the lower surface of the pin is adjacent the mounting surface on that phalange and the axis of curvature of head of the second pin is parallel to the pivotal axis of the joint. When inserting the pins into the phalanges, it is preferable to apply an adhesive to at least a portion of the pins prior to inserting the pins into the phalanges. Next, the spacer is placed between the first and second heads so that the bearing surfaces on the spacer align with the bearing surface on the heads to enable the prosthesis to flex and extend in a first plane while constraining abduction, adduction and rotation of the prosthesis.

When a multiplicity of spacers with various depths are provided, a spacer should be selected with a depth appropriate to provide proper tension in the ligaments surrounding the prosthesis. This determination is often made after the first and second pins are inserted into the ends of the phalanges, so that the distance between the pins may be measured before selecting a suitable spacer. In addition, when a multiplicity of pins are provided, the pins should be selected so that they closely correspond to the size and configuration of the ends of the phalanges that are resected.

It will now be clear that an improvement in this art has been provided which accomplishes the objectives set forth above. While the invention has been disclosed in its preferred form, it is to be understood that the specific embodiments which have been depicted and described are not to be considered in a limited sense because there are other forms which should also be construed to come within the scope of the appended claims.

I claim:

1. A phalangeal finger joint prosthesis, comprising:
    a first pin having an elongate shaft for inserting into a proximal end of a phalange on a first side of a finger joint, the first pin further including a head with a lower surface mounted on the shaft and a convex cylindrically-shaped bearing surface that is opposite the lower surface and defines an axis of curvature;
    a second pin having an elongate shaft for inserting into a distal end of a phalange on a second side of the finger joint, the second pin further including a head with a lower surface mounted on the shaft and a convex cylindrically-shaped bearing surface that is opposite the lower surface and defines with an axis of curvature; and
    a spacer configured to be disposed between the heads of the first and the second pins, the spacer having opposed bearing surfaces that are each configured to mate with the bearing surface of one of the heads so that the bearing surfaces of the heads are generally oriented toward each other, the spacer configured to couple the first and the second pins in a spaced relationship with parallel axes of curvature to permit the prosthesis to flex and extend in a single plane while constraining abduction, adduction and rotation of the prosthesis.

2. The prosthesis of claim 1, wherein each of the bearing surfaces on the spacer includes a race along which the beating surface of one of the heads is received and can slidably pivot about its axis of curvature.

3. The prosthesis of claim 1, wherein each of the bearing surfaces on the spacer has a concave cylindrical configuration that corresponds to the configuration of the bearing surface of the head that it receives.

4. The prosthesis of claim 1, wherein each head includes a side wall extending around the perimeter of the head adjacent its beating surface.

5. The prosthesis of claim 1, wherein the shafts are conically tapered inwardly along their lengths as they extend away from the heads.

6. The prosthesis of claim 1, wherein the lower surface of each pin has a generally planar configuration.

7. The prosthesis of claim 1, wherein each head is configured to correspond generally to the shape of an end of a phalange.

8. The prosthesis of claim 1, wherein each of the bearing surfaces on the pins has generally linear edges parallel to its axis of curvature and generally arcuate edges transverse to its axis of curvature.

9. A phalangeal finger joint prosthesis for replacing a joint between two adjacent phalanges with articulating ends, the prosthesis comprising:

a pair of opposed bone-engaging members, each member having a lower surface configured to be mounted on the end of one of the phalanges and a convex, cylindrically-shaped bearing surface that is opposite the lower surface and defines an axis of curvature; and a spacer configured to be disposed between the bearing surfaces of the bone-engaging members, the spacer having opposed bearing surfaces that are each configured to receive the cylindrical beating surface of one of the heads so that the bearing surfaces of the heads are generally facing each other, the spacer configured to couple the first and the second bone-engaging members in a spaced relationship with parallel axes of curvature and to permit the prosthesis to flex and extend in a single plane while constraining abduction, adduction and rotation of the prosthesis.

10. The prosthesis of claim 9, wherein the bearing surfaces of the spacer each defines a race along which the bearing surface of one of the bone-engaging members is received and can slidably pivot about its axis of curvature.

11. The prosthesis of claim 9, wherein the beating surfaces of the bone-engaging members have generally convex cylindrical configurations.

12. The prosthesis of claim 9, wherein the lower surface of each of the bone-engaging members has a generally planar configuration.

13. The prosthesis of claim 9, wherein each bone-engaging member includes a side wall extending around the perimeter of the bone-engaging member between the bearing surface and the lower surface.

14. The prosthesis of claim 9, wherein each bone-engaging member is configured to correspond generally to the shape of an end of a phalange.

15. The prosthesis of claim 9, wherein each beating surface on the bone-engaging members has generally linear edges parallel to its axis of curvature and generally arcuate edges transverse to its axis of curvature.

16. A phalangeal finger joint replacement kit, comprising:

a first pin having an elongate shaft for inserting into a proximal end of a phalange on a first side of a finger joint, the first pin further including a head with a lower surface mounted on the shaft and a convex cylindrically-shaped bearing surface that is opposite the lower surface and defines an axis of curvature;

a second pin having an elongate shaf for inserting into a distal end of a phalange on a second side of the finger joint, the second pin further including a head with a lower surface mounted on the shaf and a convex cylindrically-shaped bearing surface that is opposite the lower surface and defines with an axis of curvature; and a multiplicity of spacers that are configured to be disposed between the heads of the first and the second pins, each spacer having opposed bearing surfaces that are configured to mate with the bearing surface of one of the heads so that the bearing surfaces of the heads are generally oriented toward each other and coupled in a spaced relationship with parallel axes of curvature to form a finger joint prosthesis and to permit the prosthesis to flex and extend in a single plane while constraining abduction, adduction and rotation of the prosthesis, the spacers having various depths, measured as the shortest distance between the bearing surfaces of the spacer.

17. The kit of claim 16, wherein each of the bearing surfaces of the spacers defines a race along which the bearing surface of one of the heads is received and can slidably pivot about its axis of curvature.

18. The kit of claim 16, wherein each bearing surface on the spacer has a concave cylindrical configuration that corresponds to the configuration of the bearing surface of the head that it receives.

19. The kit of claim 16, wherein each head includes a side wall extending around the perimeter of the head adjacent the its bearing surface.

20. The kit of claim 16, wherein the shafts are cortically tapered inwardly along their lengths as they extend away from the heads.

21. The kit of claim 16, wherein the lower surface of each pin has a generally planar configuration.

22. The kit of claim 16, wherein each head is configured to generally correspond to the shape of an end of a phalange.

23. The kit of claim 16, wherein the bearing surface on each head has generally linear edges parallel to its axis of curvature and generally arcuate edges transverse to its axis of curvature.

24. A method for replacing a phalangeal finger joint that includes adjacent phalanges with articulating ends that define a pivotal axis, the method comprising:

resecting at least a portion of the articulating ends of the phalanges to form mounting surfaces;

providing a pair of opposed pins, which each have a shaft configured to extend into the end of one of the phalanges and a head with lower surface mounted on the end and a convex, cylindrically-shaped bearing surface that is opposite the lower surface and defines an axis of curvature, and a spacer configured to be disposed between the bearing surfaces of the bone-engaging members, the spacer having opposed bearing surfaces that are each configured to receive the cylindrical bearing surface of one of the heads so that the bearing surfaces of the heads are generally oriented toward each other and coupled in a spaced relationship with parallel axes of curvature to form a finger joint prosthesis and to permit the prosthesis to flex and extend in a single plane while constraining abduction, adduction and rotation of the prosthesis;

inserting the shaft of a first pin into the end of one of the phalanges so that the lower surface of the first pin is adjacent the mounting surface on that phalange and the axis of curvature of the bearing surface is parallel to the pivotal axis of the joint;

inserting the shaft of the other pin into the end of the other phalange so that the lower surface of the corresponding pin is adjacent the mounting surface on that phalange and the axis of curvature of the head is parallel to the pivotal axis of the joint; and placing the spacer between the heads of the pins so that the bearing surfaces on the spacer align with the bearing surfaces on the heads to permit the prosthesis to flex and extend in a first plane while constraining abduction, adduction and rotation of the prosthesis.

25. The method of claim 24, wherein the inserting steps include the substep of applying an adhesive to at least a portion of the pins prior to inserting the pins into the phalanges.

26. The method of claim 24, wherein the providing step includes providing a multiplicity of spacers that have various depths, measured as the shortest distance between the bearing surfaces of each spacer, and the placing step is preceded by the step of selecting a spacer with a depth appropriate to provide desired tension to the prosthesis.

27. The method of claim 26, wherein the inserting steps include the substep of applying an adhesive to at least a portion of the pins prior to inserting the pins into the phalanges.

* * * * *